(12) United States Patent
Elliott et al.

(10) Patent No.: US 6,198,802 B1
(45) Date of Patent: Mar. 6, 2001

(54) SCANNING BEAM X-RAY SOURCE AND ASSEMBLY

(75) Inventors: Douglas D. Elliott, Scotts Valley; Peter E. Loeffler, Los Gatos; David E. Baker, San Jose; Brian Skillicorn, Saratoga, all of CA (US)

(73) Assignee: Cardiac Mariners, Inc., Los Gatos, CA (US)

( * ) Notice: Subject to any disclaimer, the term of this patent is extended or adjusted under 35 U.S.C. 154(b) by 0 days.

(21) Appl. No.: 09/167,399

(22) Filed: Oct. 6, 1998

(51) Int. Cl.$^7$ ........................................ A61B 6/03
(52) U.S. Cl. .......................... 378/119; 378/101; 378/111
(58) Field of Search .................. 375/101–111, 113, 375/117, 119; 250/492.3

(56) References Cited

U.S. PATENT DOCUMENTS

| | | | |
|---|---|---|---|
| 3,499,146 | 3/1970 | Richards | 250/61.5 |
| 3,778,614 | 12/1973 | Hounsfield | 250/362 |
| 3,809,886 | 5/1974 | Cochran et al. | 250/323 |
| 3,922,552 | 11/1975 | Ledley | 250/369 |
| 3,925,660 | 12/1975 | Albert | 250/272 |
| 3,936,639 | 2/1976 | Barrett | 250/369 |
| 3,944,833 | 3/1976 | Hounsfield | 250/367 |
| 3,946,234 | 3/1976 | Hounsfield | 250/363 |
| 3,949,229 | 4/1976 | Albert | 250/401 |
| 3,973,128 | 8/1976 | LeMay | 250/445 |
| 3,983,397 | 9/1976 | Albert | 250/406 |
| 4,002,917 | 1/1977 | Mayo | 250/445 |
| 4,007,375 | 2/1977 | Albert | 250/404 |
| 4,010,370 | 3/1977 | LeMay | 250/366 |
| 4,017,730 | 4/1977 | Barrett | 250/363 |
| 4,031,395 | 6/1977 | LeMay | 250/360 |
| 4,032,787 | 6/1977 | Albert | 250/402 |
| 4,052,619 | 10/1977 | Hounsfield | 250/363 |
| 4,057,745 | 11/1977 | Albert | 313/55 |
| 4,066,902 | 1/1978 | LeMay | 250/363 |
| 4,144,457 | 3/1979 | Albert | 250/445 |
| 4,149,076 | 4/1979 | Albert | 250/402 |
| 4,259,582 | 3/1981 | Albert | 250/402 |
| 4,464,776 | 8/1984 | Erker | 378/10 |
| 4,573,179 | 2/1986 | Rutt | 378/10 |
| 4,962,513 | * 10/1990 | Schwierz et al. | 378/12 |
| 5,432,834 | * 7/1995 | Gershman | 378/196 |
| 5,479,470 | 12/1995 | Stenfors | 378/196 |
| 5,550,378 | 8/1996 | Skillicorn et al. | 250/367 |
| 5,610,967 | 3/1997 | Moorman et al. | 378/154 |
| 5,619,042 | * 4/1997 | Hughes | 378/150 |

FOREIGN PATENT DOCUMENTS

| | | | |
|---|---|---|---|
| WO 94/23458 | 10/1994 | (WO) | H01L/31/115 |
| WO 96/25024 | 8/1996 | (WO) | H05J/35/00 |
| WO 97/31335 | 8/1997 | (WO) | G06T/5/40 |

OTHER PUBLICATIONS

Philips Photonics, "xP1700 Multichannel Photomultipliers", *Xp1700 Family of Multi–channel Photomultipliers—Philips Photonic Handbook,* at least by Dec. 1993, pp. 1–15.

Digiray, "Digiray's Reverse Geometry X–ray System", *Digiray Marketing Brochure,* at least by Dec. 1992, pp. 1–2.

(List continued on next page.)

*Primary Examiner*—David V. Bruce
*Assistant Examiner*—Drew A. Dunn
(74) *Attorney, Agent, or Firm*—Lyon & Lyon LLP (57) ABSTRACT

A compact x-ray source and assembly is disclosed. The x-ray source is configured to operate without the need of a transformer within the x-ray source. Due in part to the elimination of components, and further due to the unique assembly of the x-ray source, the x-ray source is compact and can fit beneath, rather than above an x-ray transparent patient table. Accordingly, the x-ray source projects x-rays in an upwardly direction toward the object to be imaged. As a result of the unique configuration of the x-ray source, scattered x-rays are directed away from upper body areas of attending medical staff and radiation to the sensitive tissue of a patient is reduced.

23 Claims, 11 Drawing Sheets

OTHER PUBLICATIONS

Dolby et al., "A Spectrometer System for Long Wavelength X–ray Emission Microanalysis", *X–ray Microscopy and X–ray Microanalysis,* at least by Dec. 1960, pp. 351–357.

Brody, "Conference on Digital Radiography", *SPIE Proceedings,* Sep. 14–16, 1981, pp. 1–8.

Howard Pattee, Jr., "Possibilities of the Scanning X–Ray Microscope", at least by Dec., 1957, *X–Ray Microscopy and Microradiography,* pp. 367–375.

Maravilla, et al., "Digital Tomosynthesis: Technique for electronic Reconstructive Tomography", *American Journal of Neuroradiology,* Jul./Aug. 1983, pp. 883–888.

George L. Clark, *The Encyclopedia of X–rays and Gamma Rays,* at least by Dec. 1963, pp. 608–611.

Barrett et al., "The Theory of Image Formation, Detection, and Processing", vol. 2, *Radiological Imaging,* published at least by Dec., 1981, pp. 368–371.

Curry et al., *Christensen's Physics of Diagnostic Radiology,* Fourth Edition, Lea & Febiger, 1990, pp. 1–522.

\* cited by examiner

SCANNING BEAM X-RAY SOURCE AND ASSEMBLY

BACKGROUND OF THE INVENTION

1. Field of the Invention

The present invention pertains to the field of x-ray imaging systems, including among other things, x-ray sources for diagnostic x-ray imaging systems.

2. Background

Real-time x-ray imaging is increasingly being utilized by medical procedures as therapeutic technologies advance. For example, many electro-physiologic cardiac procedures, peripheral vascular procedures, PTCA procedures (percutaneous transluminal catheter angioplasty), urological procedures, and orthopedic procedures benefit from the use of real-time x-ray imaging.

A number of real-time x-ray imaging systems are known. These include fluoroscope-based systems where x-rays are projected into an object to be x-rayed and shadows caused by relatively x-ray opaque matter within the object are detected on the fluoroscope located on the opposite side of the object from the x-ray source.

Reverse-geometry x-ray imaging systems are also known. In such systems, an x-ray tube is employed to generate x-ray radiation. Within the x-ray tube, high-energy charged particles are generated and focused on a small spot on the relatively large target of the tube, inducing x-ray radiation emission from that spot. The charged particles are deflected (electromagnetically or electrostatically) in a raster scan pattern or otherwise over the target. A small x-ray detector is placed at a distance from the target of the x-ray tube. The detector typically converts x-rays that strike it into an electrical signal in proportion to the detected x-ray intensity.

Known embodiments of x-ray imaging systems place the x-ray source above the patient, wherein each of the component parts of the x-ray scanning tube assembly are stacked on top of the other components, one component after another (e.g., from bottom to top, a vacuum envelop assembly below a charged particle generator, the charged particle generator below a high-voltage terminal assembly, etc.) In these systems, a high-voltage power supply receptacle is connected to the high-voltage terminal assembly with the longitudinal axis of the high voltage receptacle parallel with the projection axis of the charged particle generator.

When the x-ray imaging system is activated and radiation is projected from the x-ray scanning tube, the radiation is generally in a downward direction and some of the radiation scatters off the patient and the x-ray table supporting the patient. Since the radiation is in a generally downward direction the scattered radiation is directed predominantly in an upward direction towards the most sensitive portions of the body of the attending staff, namely the head and neck. Furthermore, since patients usually lie face up on an x-ray table, when a woman is being imaged, her breast tissue which is typically more sensitive than most other tissue types, is subjected to the direct radiation from the x-ray source.

Thus, there is a need for an x-ray imaging system that will minimize the risks to the patient and the attendant staff, as well as allow the x-ray imaging system to be more useful.

SUMMARY OF THE INVENTION

A compact x-ray source and assembly is disclosed. An embodiment of the present invention comprises an x-ray source wherein a high-voltage receptacle comprises a receptacle axis defined by the longitudinal axis of the high-voltage receptacle and a charged particle gun comprises a projection axis and a projection plane perpendicular to the projection axis. The high voltage receptacle and the charged particle are arranged such that an angle is formed between the receptacle axis and the projection plane, wherein the angle (which is the smallest angle formed by the intersection between the receptacle axis and projection plane) is less than 75 degrees.

According to another embodiment, power to the gun electronics is provided without the need for a transformer.

These and other objects, advantages, and aspects of the present invention will become apparent to those of ordinary skill in the art from a consideration of the drawings, description, and claims of the invention contained herein.

BRIEF DESCRIPTION OF THE DRAWINGS

Preferred embodiments of the present invention are illustrated by way of example, and not by way of limitation, in the figures of the accompanying drawings and in which, like reference numerals refer to similar elements and in which.

DETAILED DESCRIPTION

Figure 1:
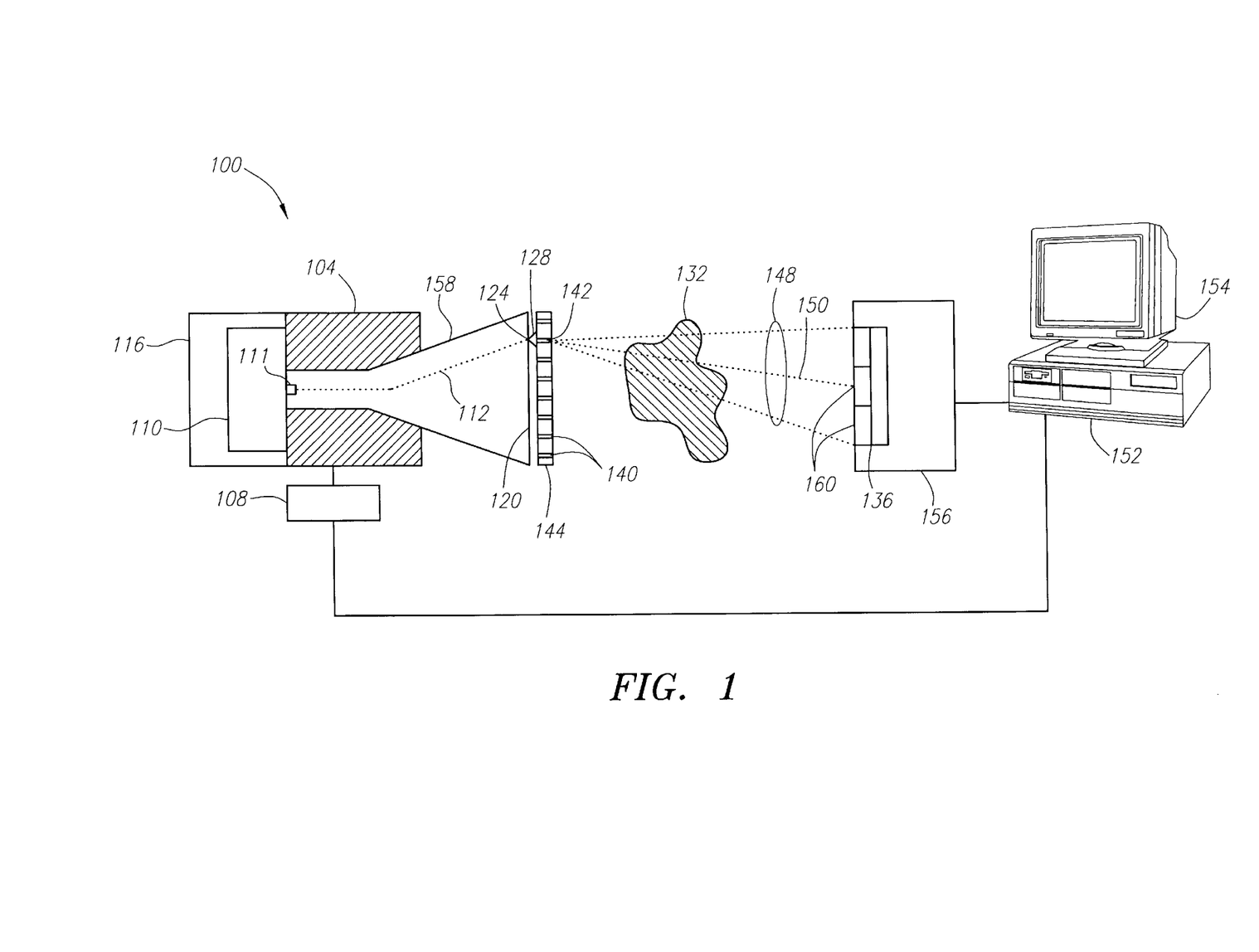
FIG. 1 is a block diagram showing the basic components of an x-ray imaging system.

FIG. 1 depicts an embodiment of a presently preferred x-ray imaging system. The x-ray source 100 preferably comprises an x-ray tube and a high-voltage charged particle source. The high-voltage charged particle source is preferably connected to an adjustable high-voltage power supply capable of generating approximately −70 kV to −120 kV.

According to a preferred embodiment, the high-voltage power supply provides a DC output to the x-ray imaging system. At this voltage level, x-ray source 100 produces a spectrum of x-rays ranging to 120 keV. X-ray source 100 is an example of a scanning beam x-ray source in which the charge particle beam is scanned across a target assembly. X-ray source 100 preferably includes deflection coils 104 under the control of a scan generator 108. High-energy charged particles 112 generated within vacuum chamber 158 by gun 111 are scanned across a target assembly 120 in a predetermined pattern. For example, the predetermined pattern may be a raster scan pattern, a serpentine (or "S" shaped) pattern, a spiral pattern, a random pattern, or such other pattern as may be useful to the task at hand. The predetermined pattern may be a "stepping" pattern in which the high-energy charged particles 112 are dwelled at a particular location on the target assembly 120 for a period of time before being moved to dwell at other locations on the target assembly 120. An apparatus that can be used in an embodiment of the invention for generating and moving charged particles across target assembly 120 is disclosed in commonly owned U.S. Pat. No. 5,644,612, which is incorporated herein by reference in its entirety.

Charged particles 112 pass through vacuum chamber 158 and strike target assembly 120 at focal spot 124. X-rays 128 are emitted in all directions (although the term "x-rays" are used herein, it is for illustration purposes only—other forms of radiation can be employed according to the present invention.) For simplicity, only a portion of the x-rays 128 are shown. The x-rays 128 preferably pass through a collimator toward the object 132 to be investigated. To optimize system performance of a presently preferred embodiment, x-rays are generated that diverge in a manner that just covers the detector 136. This is preferably accomplished by placing a collimating element between the target assembly 120 of the x-ray source 100 and the detector 136, and more preferably between object 132 and x-ray source 100. According to one embodiment, the x-rays 148, after passing through collimation grid 144, only diverge slightly from axis 150.

The presently preferred configuration for the collimating element is a grid of x-ray transmissive cylinders or apertures 140. Collimation grid 144 is designed to permit passage to only those x-rays whose axes are in a path (e.g. axis 150) that directly intersects the detector 136. Collimation grid 144 preferably does not move with respect to the detector 136 while the system is in operation. Thus, as charged particles 112 are scanned across target assembly 120, at any given moment there is only a single beam of x-rays 148 which pass through object 132 to detector 136. According to one embodiment, detector 136 has a face having an area, wherein the area is broken into individual segments 160. Each segment is a detector which, when combined, form a detector array, simply referred to as detector 136. A collimation grid 144, useful in an embodiment of the invention, is disclosed in commonly owned U.S. Pat. No. 5,859,893, which is incorporated herein by reference in its entirety.

The output of detector 136 is processed by an image reconstruction system 156 and displayed by a video display device 154 which is preferably attached to a workstation 152. The video display device 154 allows attending staff to view the x-ray images.

Figure 10:
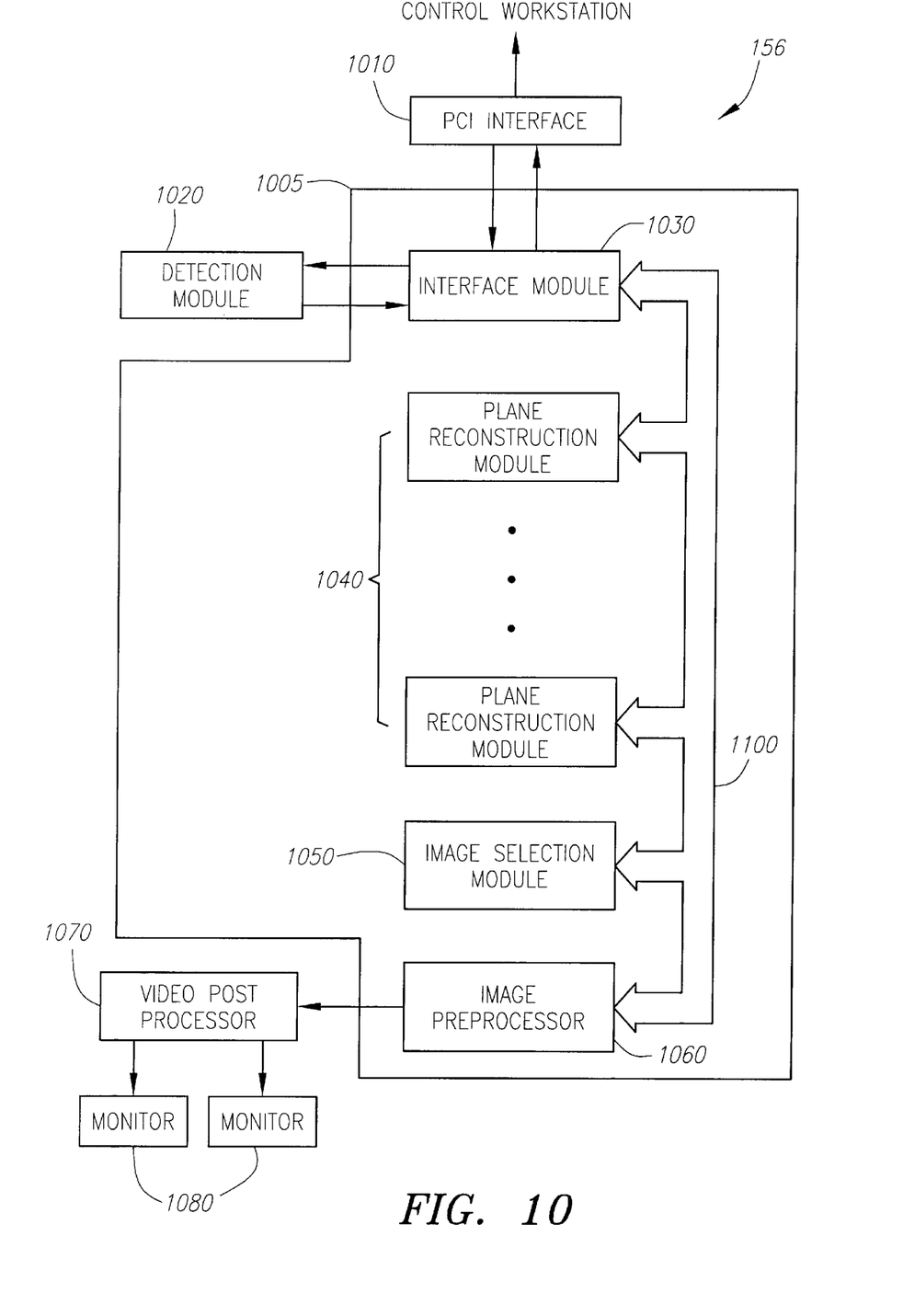
FIG. 10 is a block diagram of a preferred imaging system.

FIG. 10 depicts a block diagram of an embodiment of the image reconstruction system 156. The image reconstruction system 156 comprises a PCI interface 1010, which connects to control workstation 152. A detection module 1020 comprises the components of detector 136 and receives x-ray transmissiveness information. Image reconstruction chassis 1005 comprises an interface module 1030, one or more plane reconstruction modules 1040, an image selection module 1050 and an image preprocessor 1060. The various components on the image reconstruction chassis 1005 are interconnected via one or more busses 1100, which also include control lines. PCI interface 1010 and detection module 1020 are coupled to interface module 1030, whereas image preprocessor 1060 is coupled to video post processor 1070. Video post processor 1070 is coupled to display monitors 1080.

Details of the presently preferred embodiments of the components depicted with reference to FIG. 10 are described in detail in copending U.S. patent application Ser. Nos. 09/167,318, 09/167,397, 09/167,171, 09/167,413, all of which are incorporated herein by reference in their entirety.

According to a preferred embodiment, information about the x-rays 148 detected at the detector 136 is fed back to scan generator 108. Accordingly, the workstation 152 and the scan generator 108 are coupled.

Details of presently preferred embodiments of the elements depicted in FIG. 1, as well as elements related to the same, are described in further detail in copending U.S. patent application Serial Nos. 09/167,524, 09/167,405, 09/167,523 and 09/167,639, filed on the same day herewith, all of which are incorporated herein by reference in their entirety.

Figure 2:
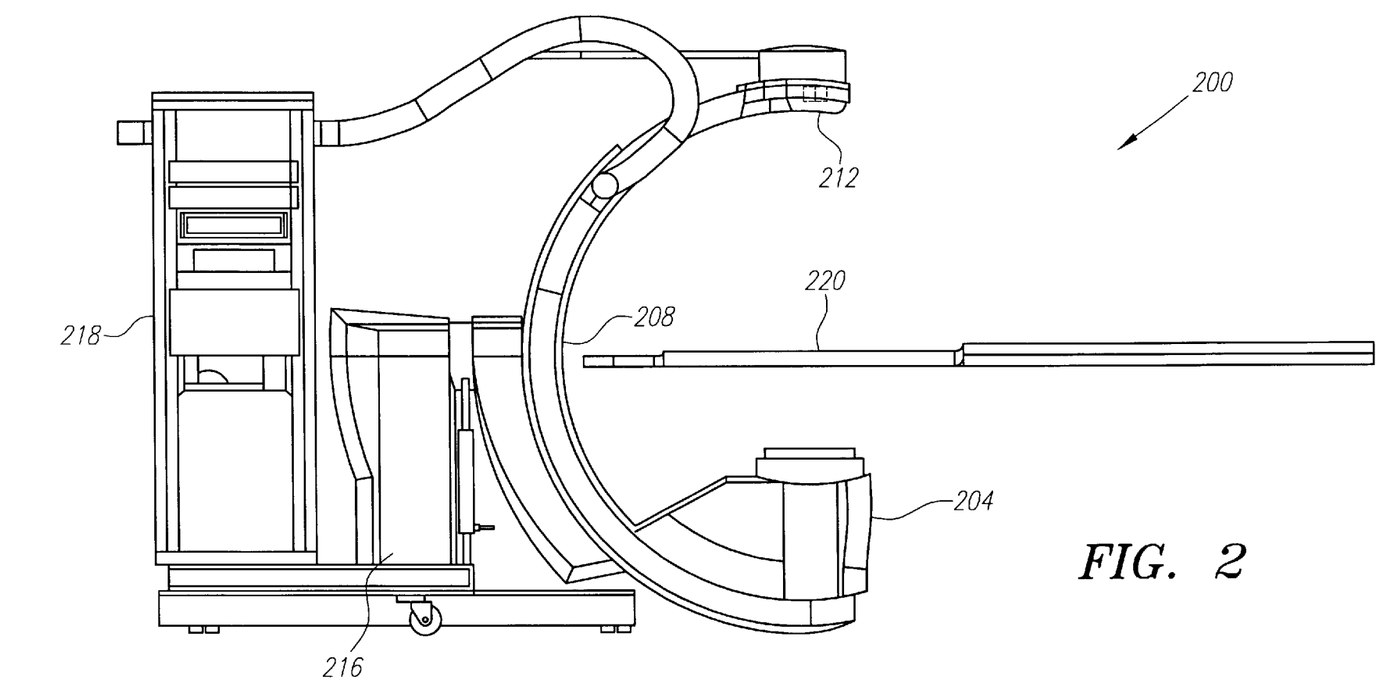
FIG. 2 is a side-view of a preferred x-ray imaging system.

FIG. 2 is a side view of a presently preferred x-ray imaging system 200. X-ray imaging system 200 comprises an x-ray source 204 connected to one end of a curved gantry 208. At a second end of curved gantry 208 is attached a detector 212. According to one embodiment, the curved gantry 208 is attached to a base support 216. The gantry 208 is preferably capable of spherical movement.

X-ray table 220, preferably having one or more x-ray transparent areas, supports an object for which an x-ray image is desired. According to an embodiment of the x-ray table 220, the x-ray table 220 can be a substantially flat table, having no dips or valleys. However, according to another embodiment it may include one or more dips or valleys to more approximately match the general shape of the object being imaged. The x-ray source 204 is preferably located at the end of the gantry that is capable of movement in the lower hemisphere.

According to one embodiment, cabinet 218 supports a control workstation and display device (e.g., control workstation 152 and monitor 154).

Figures 3A, 3C:
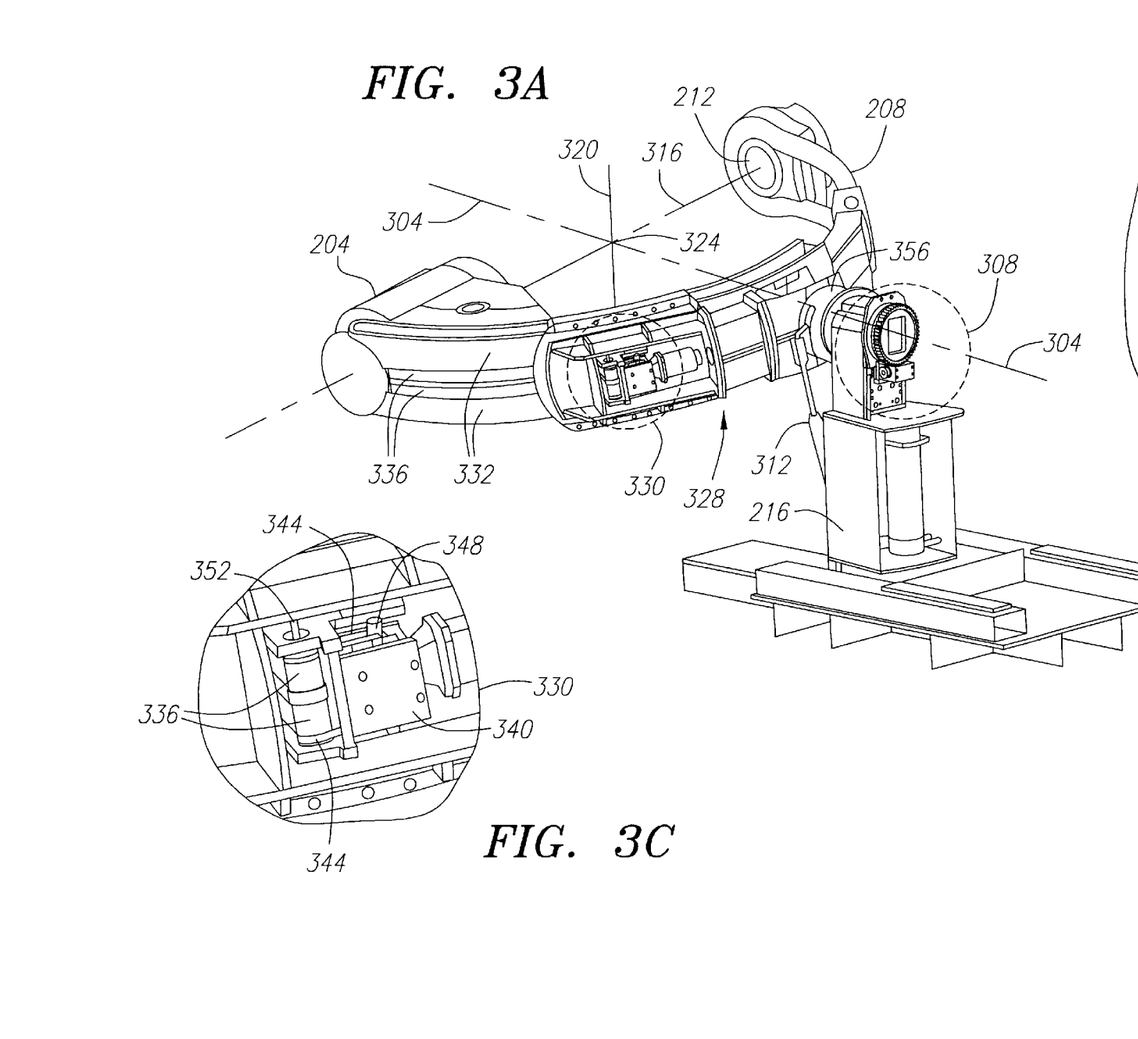
FIG. 3A is a perspective view of a preferred x-ray imaging system shown rotated to facilitate explanation.
FIG. 3C is a perspective view of an angulation mechanism according to one embodiment of a preferred x-ray imaging system.
Figure 3B:
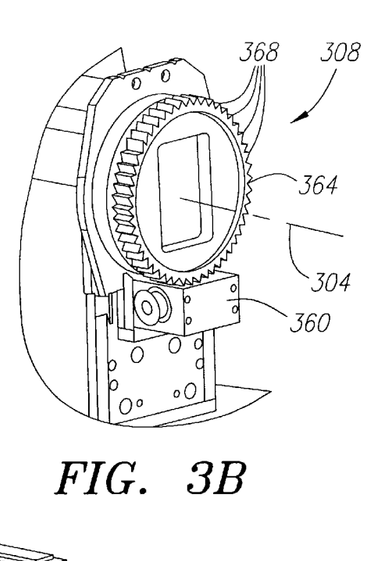
FIG. 3B is a perspective view of a rotator mechanism according to one embodiment of a preferred x-ray imaging system.

FIGS. 3A–C depict, in greater detail, embodiments of mechanisms that facilitate the hemispherical movement of the gantry 208 as is known in the art.

In FIG. 3A, gantry 208 is depicted rotated about a rotational pivot axis 304. Rotator mechanism 308, depicted in further detail in FIG. 3B and described below, supports gantry 208 and provides a force to drive gantry 208 about axis 304. In addition, a hydraulic support arm 312 further supports the load and rotation of gantry 208 as it is rotated about axis 304 by rotator mechanism 308.

According to a preferred embodiment, gantry 208 is further configured to slide along a curved path concentric with a curve following the shape of gantry 208. Projection axis 316, formed between x-ray source 204 and detector 212, and pivot axis 304 intersect at point 324. Angulation axis 320 is perpendicular to projection axis 316 and pivot axis 304. Angulation mechanism 328 provides support and force to slide gantry 208 such that gantry 208 slides in a circular or curved path about angulation axis 320. According to one embodiment, angulation mechanism 328 comprises bearing rails 332 and two drive belts 336. According to one embodiment, the bearing rails 332 also provide support for gantry 208.

An enlarged view of the circled area 330 of angulation mechanism 328 is depicted in FIG. 3C. Angulation mechanism 328 further comprises an electromechanical actuator 340 and belt drives 344. Electro-mechanical actuator 340 rotates a drive wheel 348. Drive wheel 348 is connected via the belt drives 344 to roller 352 around which drive belts 336 are connected with tension. A control signal (not shown) is received by angulation mechanism 328 which, in turn, causes actuator 340 to begin to rotate drive wheel 348 and consequently drive belts 336 begin to move. As drive belts 336 move, they carry gantry 208 along the path formed by bearing rails 332, or in other words, in a curved path about angulation axis 320.

Turning to FIG. 3B, it depicts in further detail rotation mechanism 308. Rotation mechanism 308 is connected to gantry 208 via a rotational support member 356 (FIG. 3A) that is connected to bearing rails 332 (FIG. 3A). The rotational support member 356 provides not only structural support between the gantry and base support 216, but also, in conjunction with a hydraulic support arm 312, rotational assistance to rotation mechanism 308. An electro-mechanical rotator actuator 360 provides force to rotate gantry 208 about rotational pivot axis 304. As the rotator actuator 360 is actuated, internal gears (not shown) within the actuator 360 turn. While the internal gears turn, teeth 368 on rotational drive gear 364 engage the internal gears of the actuator 360 and rotate rotational drive gear 364 about axis 304. Rotational drive gear 364 is connected to gantry 208 through rotational support member 356, so when rotational drive gear 364 turns so does gantry 208.

Figure 4:
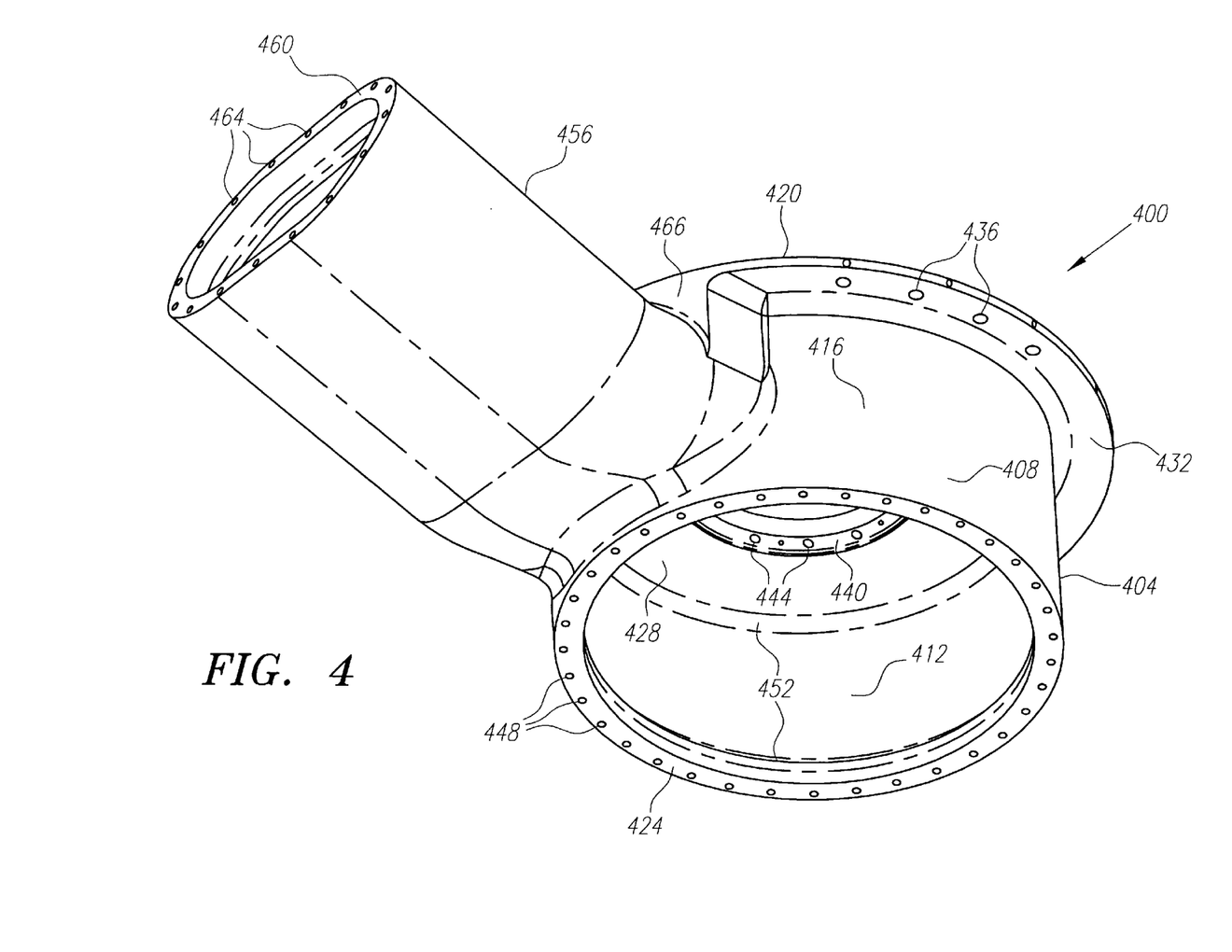
FIG. 4 is a perspective view of a preferred high-voltage vessel.

FIG. 4 depicts high-voltage vessel 400. High-voltage vessel 400 houses charged particle gun electronics (not shown) that is employed to control the charged particle gun (e.g., gun 111). Further, high-voltage vessel 400 is also configured to receive a high-voltage power supply line (not shown), which operates at a voltage potential between −70 and −120 kV. According to a preferred embodiment, high-voltage vessel 400 is also configured to receive fiber optic control lines (not shown) that are used to control the charged particle gun electronics.

Because high-voltage vessel 400 receives a high-voltage power supply line and the high-voltage vessel itself has a voltage potential at ground, the interior surface of high-voltage vessel 400 is polished and free from irregularities which may cause electrostatic discharge between the high-voltage vessel 400 and any object within the high-voltage vessel 400 that is maintained at a high-voltage (e.g., gun electronics). Additionally, sharp edges on the interior surface of the high-voltage vessel 400 are preferably chamfered or rounded to minimize the possibility of electrostatic discharge. To further protect against electrostatic discharge, high-voltage vessel 400 is sealably enclosed and designed to hold a non-conducting medium to prevent such electrostatic discharge. According to a preferred embodiment, the non-conducting medium is sulfur-hexafluoride ($SF_6$) gas. The $SF_6$ is preferably maintained in high-voltage vessel 400 at a pressure of 4 atm.

According to a preferred embodiment, high-voltage vessel 400 comprises a cylindrical chamber 404, which is larger in diameter than in height. The cylindrical chamber 404 has a chamber wall 408, an inner surface 412, an outer surface 416, a top surface 420 and a bottom surface 424. The top surface 420 of cylindrical chamber 404 preferably is connected to a washer-shaped plate 428 that creates an inner lip and an outer lip 432, with reference to the chamber wall 408. Circumferentially arranged about the outer lip 432 of plate 428 are a number of apertures 436 though which fasteners may pass. Additionally, along the inner most circumference of plate 428 is a mounting ring 440 comprising a number of evenly distributed apertures 444. The apertures 444 are designed to receive fasteners that will connect the high-voltage vessel 400 to the vacuum chamber (e.g., vacuum chamber 158).

The bottom surface 424 of cylindrical chamber 404 is preferably configured to receive a chamber cover (not shown). A number of evenly distributed cover apertures 448 are circumferentially arranged about the bottom surface 424 and allow the chamber cover to be sealably attached to the cylindrical chamber 404. When attached to bottom surface 424 of cylindrical chamber 404, the chamber cover is preferably flush with the inner surface 412 of the cylindrical chamber 404. Additionally, cylindrical chamber 404 preferably has smoothly chamfered interior edges 452.

In the broader spirit of the invention, the high-voltage vessel 400 is not limited to having a cylindrical chamber, such as cylindrical chamber 404, rather, high-voltage vessel comprises any suitable chamber configured to house a gun electronics. In this regard, the high-voltage vessel 400 can comprise, for example, a spherical chamber or an elliptical/oval chamber.

High-voltage vessel 400 preferably comprises a sleeve or tube 456, attached to the outer surface 416 of the chamber wall 408 and which creates an opening between the interior of the tube 456 and the inner surface 412 of cylindrical chamber 404. According to an embodiment, the tube 456 has an elliptical or oval shape about a longitudinal axis and a slight elbow near one end.

In an embodiment, the tube 456 and the cylindrical chamber 404 are arranged such that the longitudinal axis of tube 456 form an angle $\phi$ with a plane that is perpendicular, or substantially perpendicular to the longitudinal axis of cylindrical chamber 404. Angle $\phi$ is the smallest angle formed by the intersection between the longitudinal axis of tube 456 and the plane perpendicular to the longitudinal axis of cylindrical chamber 404. According to an embodiment, angle $\phi$ is less than 75 degrees, and in an alternate embodiment, angle $\phi$ is less than 30 degrees.

In an alternate embodiment, the longitudinal axis of the tube 456 preferably passes through the cylindrical chamber 404 to the inner surface 412 of chamber wall 408 such that the longitudinal axis of the tube 456 and the longitudinal axis of the cylindrical chamber 404 form an acute angle, as measured, generally, between the longitudinal axis of the tube 456 and a projection direction of a charged particle gun. In another embodiment the angle is substantially perpendicular, that is between approximately 60 and 120°. Finally, it should be noted that the longitudinal axis of the tube 456 and the longitudinal axis of the cylindrical chamber 404 do not have to be coaxial.

At one end of tube 456 a number of fastener apertures 464 are disposed about the outer edge 460. The fastener apertures 464 are configured to engage fasteners which secure a high-voltage feed through (not shown) to the high-voltage vessel 400. High-voltage vessel 400 preferably comprises a tube support 466 disposed between the outer lip 432 of the cylindrical chamber 404 and above the tube 456.

Figure 5:
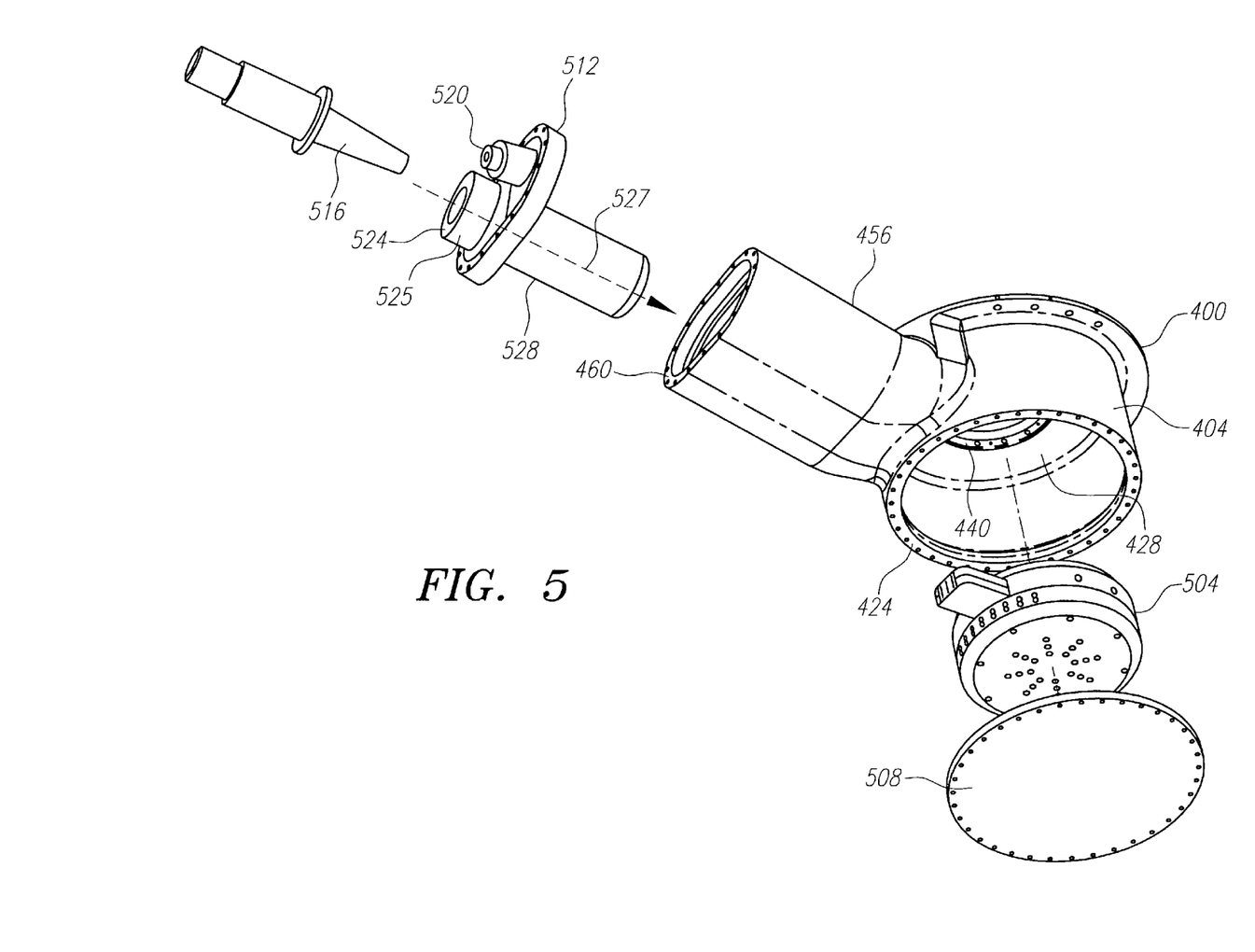
FIG. 5 is an exploded view of a preferred high-voltage vessel with components associated therewith.

FIG. 5 is an exploded view of a high-voltage vessel 400 and the components associated therewith. For example, high-voltage vessel 400 houses charged particle gun electronics 504, which is connected to the charged particle gun (not shown). A vessel cover 508 sealably encloses gun electronics 504 within the cylindrical chamber 404.

High-voltage mount 512 attaches to tube 456 at end 460. According to one embodiment, high-voltage mount 512 comprises a high-voltage receptacle 524 having a feedthrough end 525, which preferably receives one end of a −120 kV power supply line 516, a fiber optic receptacle 520, which preferably receives fiber optic control lines, and a high-voltage feedthrough 528, which shields the interior of tube 456 from the end of high-voltage power supply line 516. A receptacle vector 527 is defined by the longitudinal axis of the high voltage receptacle 524 and the direction of insertion of the high voltage cable 516 into the high voltage receptacle 524. When enclosed, high-voltage vessel 400 preferably does not allow gas to flow from the interior of the high-voltage vessel 400 out and vise-versa. A sealant or gasket may be disposed between the cover 508 and the bottom surface 424 of the cylindrical chamber 404, and the mount 512 and the end 460 of the tube 456. Fiber optic receptacle 520 is preferably sealed with or comprised of an epoxy resin.

Figure 6:
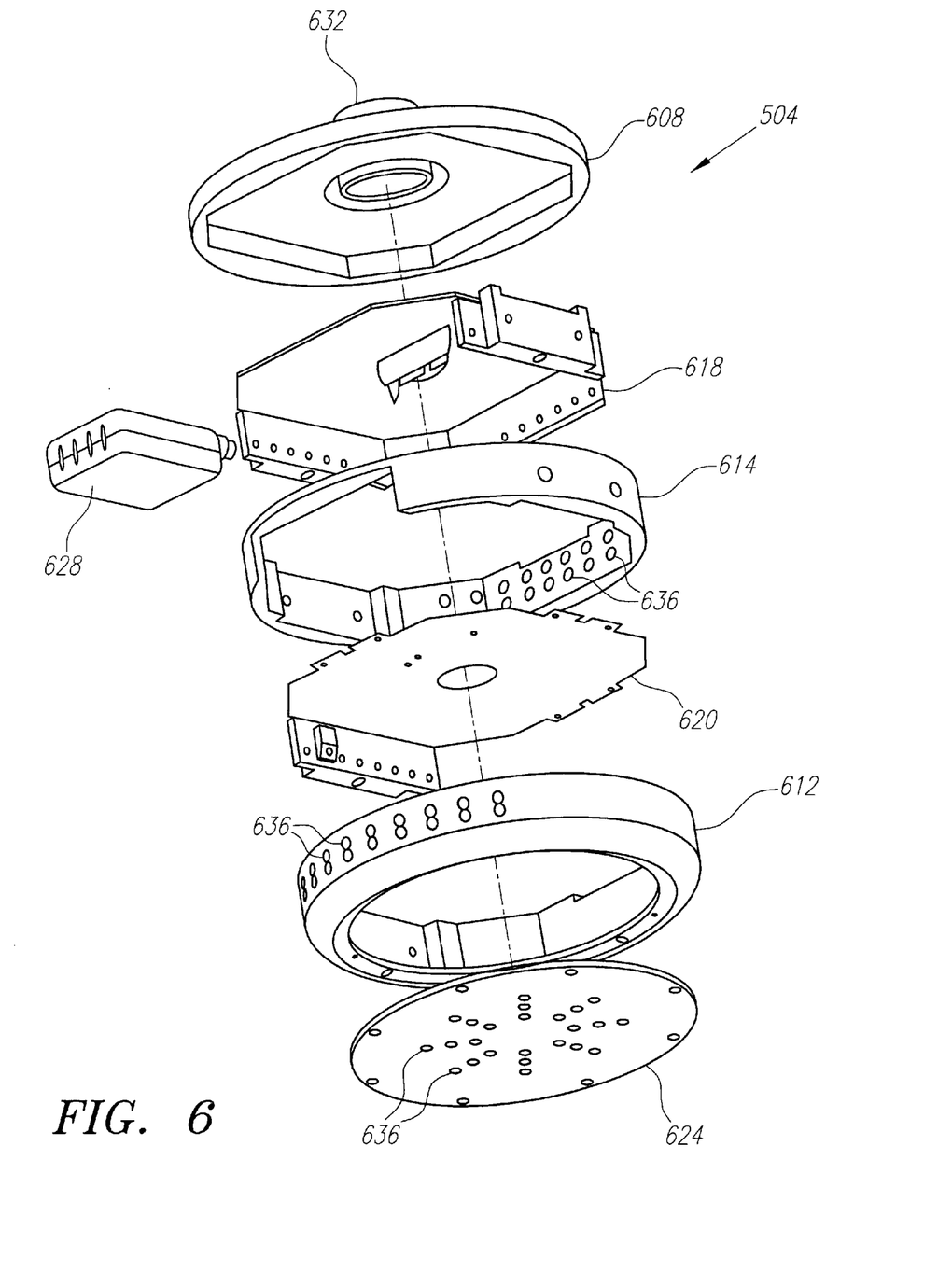
FIG. 6 is an exploded view of a preferred charged particle gun electronics.

FIG. 6 depicts an exploded view of gun electronics 504. According to one embodiment, the gun electronics 504 comprises an end cap 608, a ring housing 612 and a printed circuit board 620. The ring housing 612 mounts to the end cap 608. Disposed between the ring housing 612 and the end cap 608 is the printed circuit board 620. The printed circuit board 620 has on it control electronics to control charged the particle gun. According to another embodiment, the gun electronics 504 further comprises a mechanical ring housing 614 and, on top of the mechanical ring housing 614, a second printed circuit board 618. The mechanical ring housing 614 and the second printed circuit board 620 are disposed between the end plate 608 and the first printed circuit board 620. Further, a fiber optic and power cable connector 628 is mounted to a side of mechanical ring housing 614, and an electronics cover 624 is connected to the bottom surface of ring housing 612. The electronics cover 624, the ring housing 612 and the mechanical ring housing 614 each contain a number of openings 636 through which gas and heat may pass. Preferably, if high-voltage vessel 400 is filled with $SF_6$ gas, then the gas freely flows through the openings 636. In a preferred embodiment, a charged particle gun (not shown) is mounted to end plate 608 via a gun sleeve 632. When the x-ray source is activated, the gun is capable of projecting charged particles along the longitudinal axis of the charged particle gun and towards the target (not shown) that is above the end plate 608.

Figure 7:
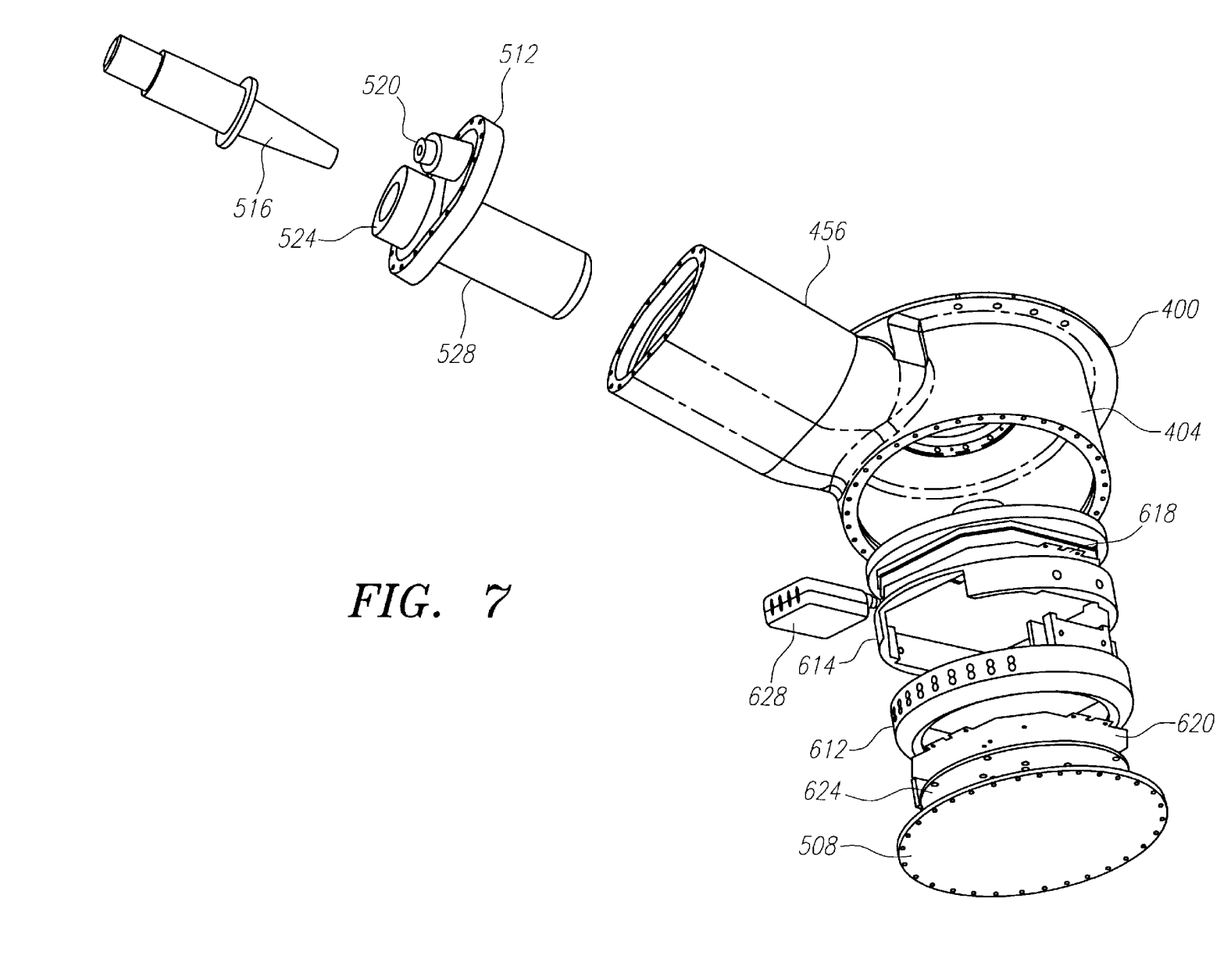
FIG. 7 is a second exploded view of a preferred high-voltage vessel with components associated therewith.

FIG. 7 is a perspective exploded view that depicts the interconnections between high-voltage vessel 400 and its associated components. According to an embodiment, once the high-voltage vessel 400 is assembled, two conducting cables (not depicted in FIG. 7) run between the high-voltage receptacle 528 and gun electronics 504 (FIG. 5). Since the gun electronics 504 does not include a power transformer to power the electronics circuits enclosed therein, power is provided by the two conducting cables, which have a voltage differential of approximately 30 V. The gun electronics 504 is maintained at approximately –100 kV during operation of the x-ray source. In addition to the two conducting cables, fiber optic cables (not shown) are also run between connector 628 and fiber optic cable receptacle 520.

Figure 8:
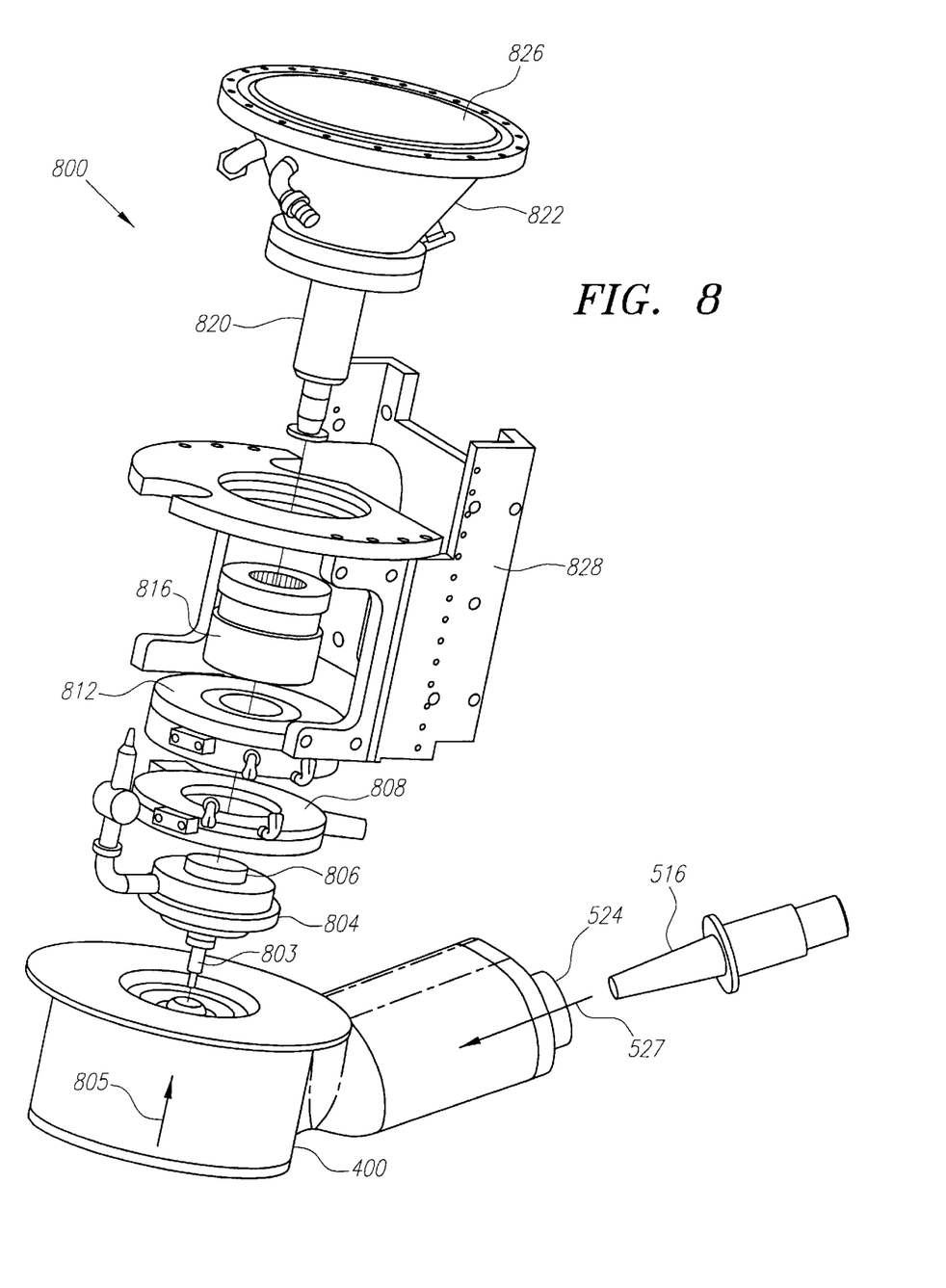
FIG. 8 is an exploded view of a preferred x-ray source.

FIG. 8 is an exploded view of a preferred embodiment of the x-ray source 800. According to the preferred embodiment, the x-ray source 800 comprises a high-voltage vessel 400, a charged particle gun, a first focus coil, a second focus coil, deflection coils, a deflection insulator, a target assembly 826 and a vacuum chamber. In one embodiment, the x-ray source is stacked, from the bottom up, such that the high-voltage vessel 400 receives an electron gun 804. Electron gun has a projection axis 803 and a projection end 806. A projection vector 805 is defined by the projection axis in a projection direction. the projection direction is from the electron gun towards the target assembly 826.

A first focus coil 808 is positioned above the electron gun 804. A second focus coil 812 is mounted on top of the first focus coil 808. A deflection insulator 820 is received by openings within the first focus coil 808, the second focus coil 812 and the deflection coils 816. The deflection insulator 820 is attached to the electron gun 804. A vacuum chamber 822 is attached to an end of the deflection insulator 820, and a target assembly 826 is placed over the vacuum chamber 822. A cradle 828, wraps around approximately three-quarters of the x-ray source 800, and extends between the top surface of high-voltage vessel 400 and approximately midway along the vacuum chamber 822. Finally, the high-voltage power cable 516 is received by high-voltage vessel 400 at high-voltage receptacle 524.

The currents flowing within first focus coil 808 and second focus coil 812 cause the charge particles 112 to be brought into focus at focal spot 124. Further, deflection coils 816 cause the charged particles 112 to track a particular scan pattern across target assembly 826.

Figure 9:
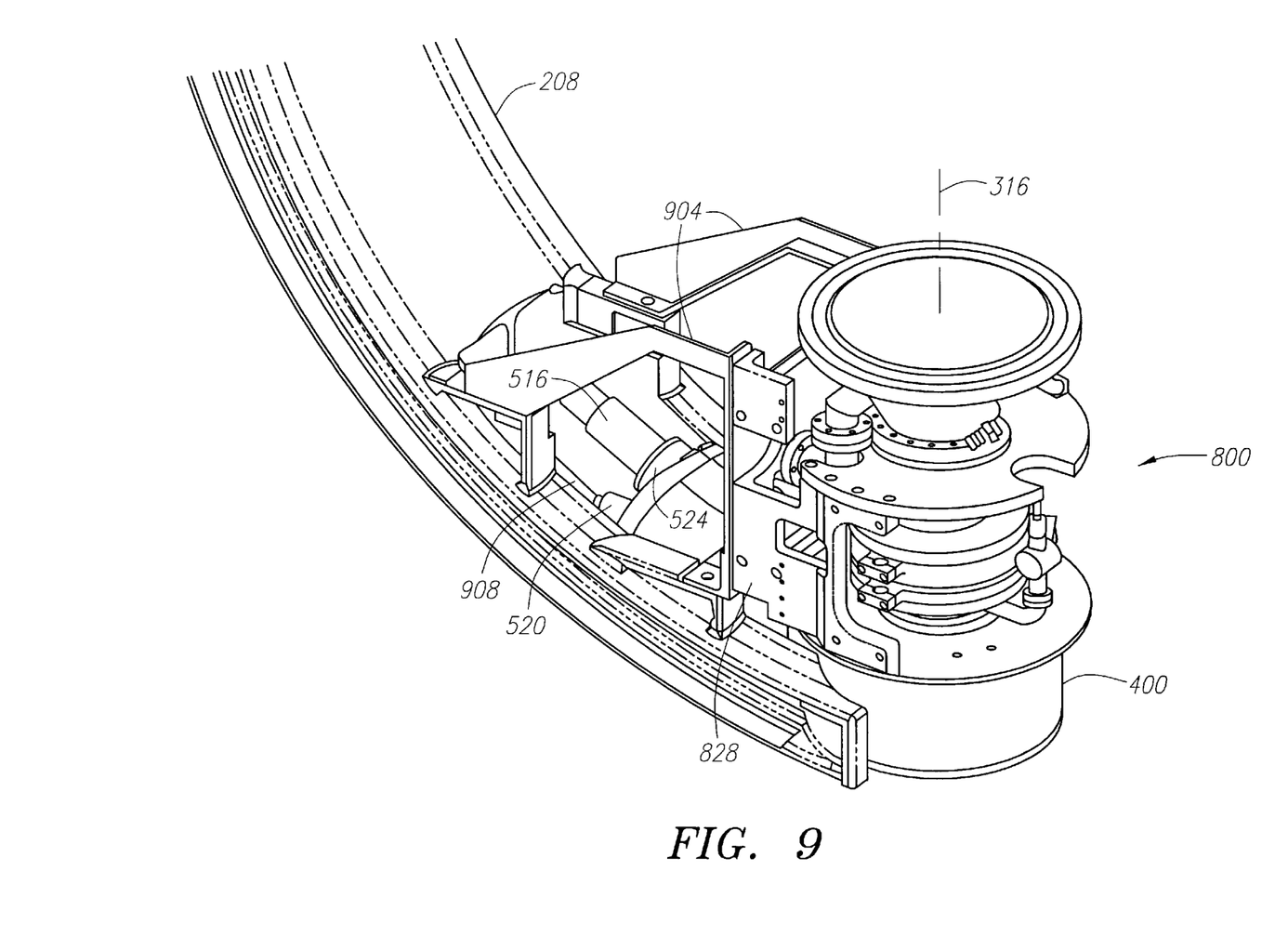
FIG. 9 is a perspective view of the x-ray source of FIG. 8 mounted on a gantry.

FIG. 9 is a perspective view of the x-ray source 800 mounted at one end of gantry 208. According to a preferred embodiment, x-ray source 800 is mounted on the lower end of gantry 208. To provide further support to x-ray source 800 as it rests on one end of gantry 208, cradle 828 is attached to gantry 208 via support arms 904. Fiber optic communication and control cables 908 are received into fiber optic cable receptacle 520. Both the fiber optic cables 908 and the high-voltage power supply line 516 are strung along the interior of gantry 208.

Figure 11:
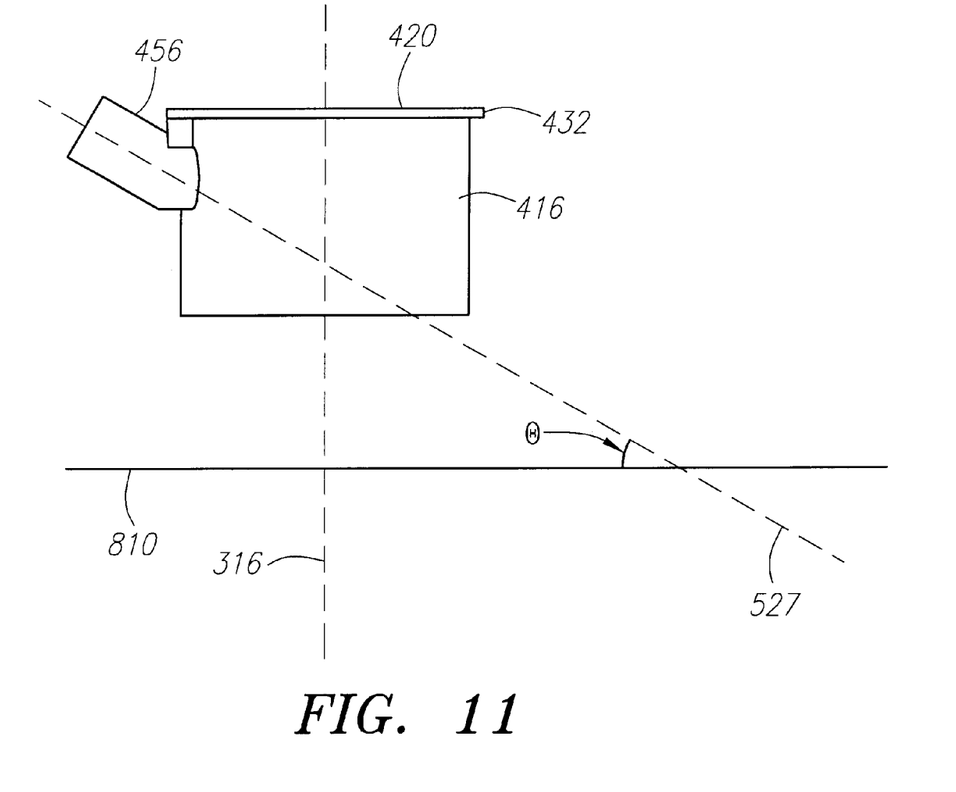
FIG. 11 is a side elevation view of FIG. 4, parallel to a projection axis.

Referring to FIG. 11, according to an embodiment, the high-voltage power supply line 516 is received into a high-voltage receptacle 524 on high voltage vessel 400 such that the longitudinal axis of high voltage receptacle 524, illustrated by receptacle vector 527, forms an angle φ with a projection plane 810 defined by the projection axis of the charged particle gun. In an embodiment, the projection plane 810 is defined as a plane perpendicular or substantially perpendicular to the projection axis of the charged particle gun and angle φ is the smallest angle formed by the intersection of the longitudinal axis (receptacle vector 527) of the high voltage receptacle 524 with the projection plane 810. In one embodiment, angle φ is less than 75 degrees, and in another embodiment, angle φ is less than 30 degrees.

In an alternate embodiment, the high-voltage power supply line 516 (FIG. 9) is received into high-voltage receptacle 524 on high-voltage vessel 400 such that the longitudinal axis (receptacle vector 527) of the high-voltage receptacle 524 forms an acute angle with the projection axis 316 of the charged particle gun, as measured between the high-voltage receptacle 524 and the charged particle gun with reference to the projection direction of the charged particle gun. Alternatively, the angle is substantially perpendicular, between approximately 60° and 120°. Finally, it should be noted that the longitudinal axis (receptacle vector 527) of the high-voltage receptacle 524 does not need to intersect the projection axis of the charged particle gun.

According to an embodiment of the innovative configuration and assembly of the x-ray source described herein, the x-ray source is compact enough to fit below, rather than above, the patient and the x-ray table 220. Consequently, when the x-ray source is activated and radiation is emitted, the x-ray scatter off the patient and x-ray table is predominantly downward, rather than upward. As a result, the risk of exposure to harmful x-rays is reduced to the attending staff, as well as depending on the procedure being performed, to the x-ray sensitive tissues of the patient. Additionally, the positioning of the x-ray source is highly adjustable, allowing movement in a spherical pattern about the x-ray table or patient.

In the foregoing specification, the invention has been described with reference to specific embodiments thereof. It will be evident, however, that various modifications and changes may be made thereto without departing from the broader spirit and scope of the invention. The specification and drawings are, accordingly, to be regarded in an illustrative, rather than a restrictive sense.

What is claimed is:

1. A scanning beam x-ray source comprising:
   a charged particle gun, said charged particle gun having a projection axis and a projection plane perpendicular to said projection axis;
   a high voltage vessel comprising a high voltage receptacle, said high voltage receptacle having a receptacle axis;
   said charged particle gun and said high voltage vessel arranged such that said receptacle axis intersects said projection plane, wherein an angle of the intersection between said receptacle axis and said projection plane is less than 75°, said angle being the smallest angle formed by said intersection.

2. The scanning beam x-ray source of claim 1 wherein said angle is less than 30°.

3. The x-ray source of claim 1, wherein said receptacle axis and said projection axis intersect.

4. The x-ray source of claim 1, further comprising a gun electronics coupled to said charged particle gun, said gun electronics receiving power from a source other than a transformer that is located within said scanning beam x-ray source.

5. The x-ray source of claim 1, said high-voltage vessel comprising:
   a cylindrical chamber having a top surface, a bottom surface, an interior surface, an outer surface, a wall and an opening, and said cylindrical chamber configured to house a gun electronics; and
   a tube having open ends, one end of said tube attached to said outer surface of said chamber wall such that the interior of said tube connects with said interior surface of said cylindrical chamber.

6. The x-ray source of claim 1, further comprising:
   a gun electronics housed within said high-voltage vessel; and
   conducting cables, disposed between said high-voltage receptacle and said gun electronics, said conducting cables configured to operate at approximately −100 kV and to provide a voltage differential of approximately 30 V to said gun electronics.

7. The scanning beam x-ray source of claim 1 further comprising a gantry, wherein said projection axis is repositioned in correspondence to repositioning of said gantry.

8. An x-ray source, comprising:
   a charged particle gun, said charged particle gun having a projection axis and a projection plane perpendicular to said projection axis;
   a high voltage vessel comprising a high voltage receptacle, said high voltage receptacle having a receptacle axis;
   said charged particle gun and said high voltage vessel arranged such that said receptacle axis intersects said projection plane, wherein an angle of the intersection between said receptacle axis and said projection plane is less than 75°, said angle being the smallest angle formed by said intersection;
   a vacuum chamber, said charged particle gun projecting charged particles in said vacuum chamber;
   a first focus coil, said first focus coil surrounding a first portion of said vacuum chamber; and
   a target assembly, said charged particles projected at said target assembly.

9. The x-ray source of claim 8 wherein said first focus coil comprises a static focus coil.

10. The x-ray source of claim 8 further comprising a second focus coil surrounding a second portion of said vacuum chamber.

11. The x-ray source of claim 10 wherein said second focus coil comprises a dynamic focus coil.

12. The x-ray source of claim 8 wherein said projection axis is within 45° of vertical.

13. The x-ray source of claim 8 wherein said angle is less than 30°.

14. The x-ray source of claim 8, wherein said high-voltage vessel comprises:
   a cylindrical chamber having a top surface, a bottom surface, an interior surface, an outer surface, a wall and an opening, said cylindrical chamber having a height which is shorter than its diameter, and said cylindrical chamber configured to house said gun electronics; and
   a tube having open ends, one end of said tube attached to said outer surface of the chamber wall such that the interior of said tube connects with the interior surface of said cylindrical chamber, and the longitudinal axis of said tube and the longitudinal axis of said cylindrical chamber are configured to form an angle of less than 120° with reference to said projection axis; and
   a high-voltage receptacle mounted to said tube, said high-voltage receptacle configured to receive the high-voltage power supply cable.

15. The x-ray source of claim 8, further comprising a high-voltage receptacle and conducting cables, said conducting cables being disposed between said high-voltage receptacle and said charged particle gun electronics, said conducting cables configured to operate at approximately −100 kV, and said conducting cables configured to supply a voltage differential of approximately 30 V to said gun electronics.

16. A high-voltage vessel, comprising:
   a gun electronics chamber, said gun electronics chamber comprising a charged particle gun projection axis and a charged particle gun projection direction; and
   a high-voltage power cable sleeve connected to said gun electronics chamber, said high-voltage power cable sleeve configured to receive a high-voltage power cable along a longitudinal axis of said high-voltage power cable sleeve, and said longitudinal axis of said high-voltage power cable sleeve intersects a line parallel to said charged particle gun projection axis to form an angle of less than 120° with reference to said charged particle gun projection direction.

17. The high voltage vessel of claim 16 wherein said gun electronics chamber comprises an interior surface, said interior surface being smooth and free of irregularities.

18. The high-voltage vessel of claim 16, wherein said gun electronics chamber is a cylindrical shape comprising a top surface, a bottom surface, an outer surface, a wall and an opening, and said gun electronics chamber is shorter in height than diameter.

19. The high voltage vessel of claim 18 wherein said high-voltage power cable sleeve is oval shaped about said longitudinal axis of said high-voltage power cable sleeve, said high-voltage power cable sleeve having an elbow bending between 10° and 30° toward the top surface of said gun electronics chamber, and said sleeve including a high-voltage receptacle and a fiber optic cable receptacle.

20. A high-voltage vessel, comprising:

a charged particle gun having a gun electronics, said gun electronics mounted in said high-voltage vessel, said charged particle gun configured to project a high-energy charged particle about a projection axis in a projection direction;

a high-voltage receptacle connected to said high-voltage vessel, said high-voltage receptacle configured to receive a high-voltage power cable along a longitudinal axis of said high-voltage receptacle such that said longitudinal axis and said projection axis are configured to form an angle of less than 120° with reference to said projection direction; and conducting cables disposed between said high-voltage receptacle and said gun electronics, said conducting cables configured to operate at approximately −100 kV, and said conducting cables configured to provide a voltage differential of approximately 30 V to said gun electronics.

21. The high-voltage vessel of claim 20, wherein said high-voltage vessel comprises:

a cylindrical chamber having a top surface, a bottom surface, an interior surface, an outer surface, a wall and an opening, said cylindrical chamber being shorter in height than diameter, and said cylindrical chamber configured to house said charged particle gun electronics; and a tube having open ends, one end of said tube attached to said outer surface of the chamber wall such that the interior of said tube connects with the interior surface of said cylindrical chamber, and said tube houses said high-voltage receptacle.

22. A high voltage vessel comprising:

a tube and a cylindrical chamber, said cylindrical chamber comprising a first longitudinal axis and a plane perpendicular to said first longitudinal axis;

said tube configured to receive a high voltage power supply line, said tube comprising a second longitudinal axis; and said tube and said cylindrical chamber arranged such that said second longitudinal axis intersects said plane, wherein an angle of the intersection between said longitudinal axis and said plane is less than 75°, said angle being the smallest angle formed by said intersection.

23. The high voltage vessel of claim 22 wherein said angle is less than 30°.

\* \* \* \* \*